(12) United States Patent
Fordham et al.

(10) Patent No.: US 9,579,661 B2
(45) Date of Patent: Feb. 28, 2017

(54) TRAPPING MAGNETIZABLE PARTICULATES

(71) Applicant: SCHLUMBERGER TECHNOLOGY CORPORATION, Sugar Land, TX (US)

(72) Inventors: Edmund J. Fordham, Cambridge (GB); Christopher Lenn, Kuala Lumpur (MY)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 641 days.

(21) Appl. No.: 14/038,353

(22) Filed: Sep. 26, 2013

(65) Prior Publication Data

US 2014/0091799 A1    Apr. 3, 2014

(30) Foreign Application Priority Data

Sep. 28, 2012 (GB) .................................. 1217402.5

(51) Int. Cl.
*B03C 1/02* (2006.01)
*G01R 33/28* (2006.01)
(Continued)

(52) U.S. Cl.
CPC .................. *B03C 1/02* (2013.01); *B03C 1/284* (2013.01); *B03C 1/286* (2013.01); *B03C 1/288* (2013.01);
(Continued)

(58) Field of Classification Search
CPC ............ B03C 1/02; B03C 1/284; B03C 1/286; B03C 1/288; B03C 2201/18; G01N 24/081; G01R 33/28
See application file for complete search history.

(56) References Cited

U.S. PATENT DOCUMENTS 2,830,705 A   4/1958  Johannesen
3,191,119 A   6/1965  Singer
(Continued)

FOREIGN PATENT DOCUMENTS

CN   2462213 Y   11/2001
GB   2098498 A   11/1982
(Continued)

OTHER PUBLICATIONS

Coombs, et al., "A novel heat engine for magnetizing superconductors", Supercond. Sci. Technol., vol. 21, 2008, 7 pages.

*Primary Examiner* — Rodney Bonnette

(57) ABSTRACT

Nuclear magnetic resonance apparatus for measuring properties of a fluid stream flowing within a pipeline has one or more magnet systems for applying magnetic field to the fluid stream and also has means for inducing and observing magnetic resonance within the fluid stream as it passes through a said magnetic field. The apparatus may also include a polarizing magnetic field upstream of the magnetic field in which resonance is observed. The fluid stream may be hydrocarbon from an underground reservoir. In order to guard against accumulation of magnetisable iron debris particles entrained in the fluid flow, the apparatus comprises one or more upstream traps having a magnetic field to attract and hold solid magnetizable material and an exit path for the removal of the solid magnetizable material so that it does not continue towards any polarizing field and the field where resonance is observed.

13 Claims, 4 Drawing Sheets

(51) Int. Cl.
   *B03C 1/28*      (2006.01)
   *G01N 24/08*     (2006.01)
(52) U.S. Cl.
   CPC ............. *G01N 24/081* (2013.01); *G01R 33/28* (2013.01); *B03C 2201/18* (2013.01)

(56) References Cited

U.S. PATENT DOCUMENTS

| | | |
|---|---|---|
| 3,419,715 A | 12/1968 | Stanley |
| 4,259,638 A | 3/1981 | Krueger |
| 5,684,399 A | 11/1997 | Bayer |
| 6,046,587 A | 4/2000 | King et al. |
| 6,833,069 B1 * | 12/2004 | Asterlin ................. B03C 1/284 |
| | | 15/256.5 |
| 7,008,486 B2 | 3/2006 | Corver |
| 7,501,819 B2 | 3/2009 | Ong |
| 7,852,074 B2 | 12/2010 | Edwards |
| 7,872,474 B2 | 1/2011 | Pusiol et al. |
| 8,056,408 B2 * | 11/2011 | Pop ...................... E21B 49/005 |
| | | 73/152.04 |
| 2004/0231699 A1 | 11/2004 | Corver |
| 2009/0242487 A1 * | 10/2009 | Vero ................. B01J 20/28009 |
| | | 210/661 |

FOREIGN PATENT DOCUMENTS

| | | |
|---|---|---|
| JP | 63053421 A | 3/1988 |
| JP | 07225006 A | 8/1995 |
| JP | 08243381 A | 9/1996 |
| JP | 2010279887 A | 12/2010 |
| WO | 2007045929 A2 | 4/2007 |
| WO | 2009137930 A1 | 11/2009 |

\* cited by examiner

TRAPPING MAGNETIZABLE PARTICULATES

CROSS-REFERENCE TO RELATED APPLICATION

This application claims priority to British Application No. GB1217402.5 filed 28 Sep. 2012, which is incorporated herein by reference in its entirety.

BACKGROUND

There have been a number of proposals to use nuclear magnetic resonance (NMR) variously referred to as magnetic resonance imaging (MRI) for examining a flowing stream of fluid in the pipeline. The fluid may be liquid hydrocarbon or a mixture of hydrocarbon and aqueous phases, such as the flow produced from an underground reservoir. Some gas may be present in the fluid. Use of NMR for such flow measuring/monitoring was disclosed in U.S. Pat. Nos. 3,191,119 and 3,419,715 and has been the subject of other patents since then, including U.S. Pat. Nos. 6,046,587, 7,501,819, 7,852,074 and 7,872,474. In a number of these documents the apparatus is shown as having a pipeline which passes through the magnetic field used (together with radiofrequency signals) to induce and observe magnetic resonance within the pipeline. The apparatus may also include polarizing magnets upstream of the magnets used to bring about magnetic resonance. NMR apparatus such as described in these documents has the attraction that it can be carried out without requiring any parts to be placed in the pipeline.

SUMMARY

This summary is provided to introduce a selection of concepts that are further described below. This summary is not intended to limit the scope of the subject matter claimed.

The present inventors have recognized that such NMR apparatus is at risk of becoming a trap for magnetizable particulate material which is present in the wellbore flow. Such particles could accumulate within a magnetic field provided by the apparatus. This may be detrimental to flow in the pipeline and/or detrimental to operation and accuracy of the NMR apparatus. The term "magnetizable material" is used here to denote material which can be drawn to and held by a magnetic field. Such materials may be ferromagnetic or ferrimagnetic and may or may not have a magnetic field of their own. Solid magnetizable material encountered in a flow of liquid may well be particles of, or containing, iron.

In the case of fluid flowing from an underground hydrocarbon reservoir, the magnetizable particulates may predominantly comprise iron debris which is small fragments of iron broken off or scraped like iron filings from the drillstring and wellbore tools and left in the wellbore while drilling and completing the well. The magnetizble material may also include small objects lost in the well and may include magnetite (mixed iron (ii) and iron (iii) oxide, $Fe_3O_4$) which is ferrimagnetic and may be present as an impurity in materials such as barite used as weighting agent.

The present inventors envisage trapping magnetizable particulates upstream of magnetic resonance equipment used to examine a flow of fluid. Disclosed herein is NMR apparatus for measuring properties of a fluid stream flowing within a pipeline (and which may originate from an underground reservoir) comprising one or more magnet systems for applying one or more magnetic fields to the fluid stream and means for inducing and observing magnetic resonance within the fluid stream as it passes through a said magnetic field, wherein the apparatus comprises one or more traps having a magnetic field to attract and hold solid magnetizable material and an exit path for the removal of the solid magnetizable material Also disclosed herein is a method of intercepting solid magnetizable material entrained in a fluid flow in a pipeline upstream of a magnetic resonance spectrometer, comprising: directing the flowing fluid upstream of the spectrometer through at least one trap having a magnetic field to attract and hold solid magnetizable material and an exit path for the removal of the solid magnetizable material.

The magnetic resonance section of the apparatus may be of known type. The apparatus may include a polarising magnetic field to polarise nuclear spins before the flowing liquid enters the magnetic field in which magnetic resonance is induced and observed. If a polarising magnetic field is provided the trapping of magnetizable solids may take place upstream of the polarizing magnetic field. As disclosed in U.S. Pat. No. 4,259,638 a polarising magnetic field may be provided by a magnet in which superconducting properties give a magnetic field of high strength. However, the constructional arrangement to incorporate a superconducting magnet may add to the inconvenience and difficulty of removing any solid magnetizable material which reaches the polarizing magnetic field, thus making it even more advantageous to intercept and remove solid magnetizable material.

A trap for magnetizable solids as disclosed herein utilises a magnetic field to arrest the travel of the magnetizable solids entrained in the fluid stream. Removal of the magnetizable solids from the path of flow may be done by taking the magnetizable solids into a branch from the pipeline and configuring this branch to provide an exit path or it may be done by temporarily disconnecting a portion of pipeline or a branch pipe in which the magnetizable solids have accumulated. Both of these approaches can remove the magnetizable material without allowing it to travel on towards a polarising magnet or the location at which magnetic resonance is induced and observed.

When removing accumulated magnetizable solids, the magnetic field which was used to arrest the magnetizable solids may be removed, for instance by moving permanent magnets or turning off an electromagnet, or the portion of pipeline or branch pipe in which the magnetizable solids have accumulated may be moved out of the magnetic field.

Trapping of magnetizable material may be carried out using a single trap, in which case the flow of liquid in the pipeline may be stopped temporarily when removal of accumulated magnetizable solids is required. Alternatively, trapping of magnetizable material may be carried out using two or more traps so that one trap is available to collect material while already-trapped material is being removed from another. One possibility is to provide two traps in parallel, with valves to direct flow selectively through one or the other. Another possibility is to provide two traps connected in sequence so that flow passes through both and each trap is configured for drawing the trapped material into an exit portion which branches off the path of flow, and allows removal of material while flow continues.

DETAILED DESCRIPTION

Embodiments of the apparatus and method disclosed herein and further features which may be used will now be described with reference to the accompanying drawings. This description is exemplary in nature and is not intended to limit the scope of the subject matter disclosed and claimed.

Figure 1:
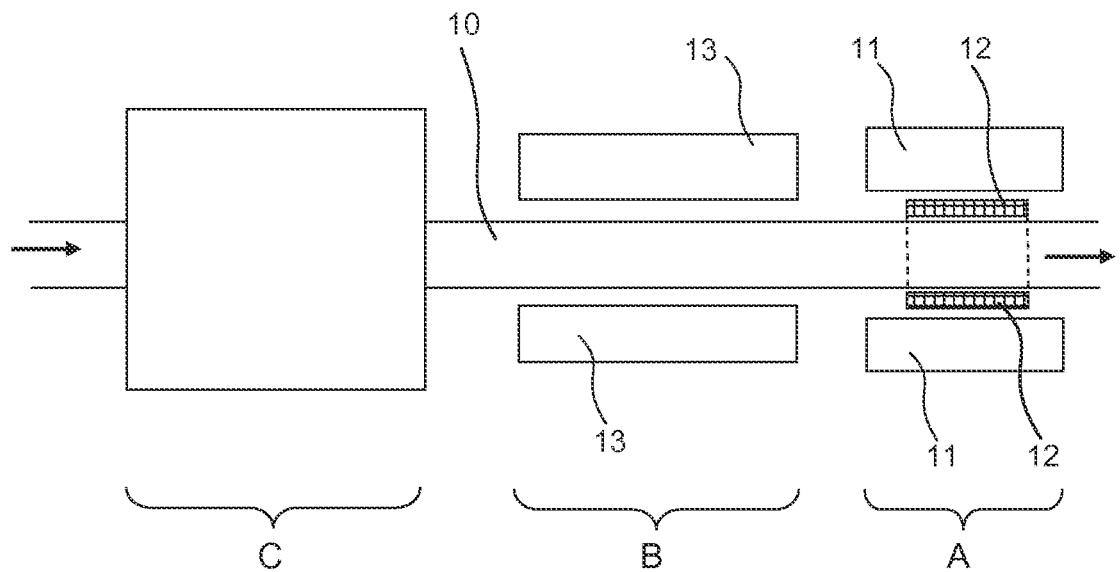
FIG. 1 is a schematic diagram of NMR apparatus including a trapping section for magnetizable particulates.

FIG. 1 shows a general arrangement of NMR apparatus for examining properties of fluid flowing along a pipeline 10 in the direction indicated by arrows. In the portion A, the pipeline 10 is made of non-magnetic electrically insulating material such as fibre reinforced polymer. The pipeline 10 extends through a uniform magnetic field between a pair of permanent magnets 11. Within this field there is at least one radio-frequency coil 12 encircling the pipeline and used to emit radiofrequency pulses to induce magnetic resonance and also to receive signals from nuclei undergoing resonance. The magnets 11, the coil 12 and associated electronics for creating radiofrequency pulses, observing radiofrequency emissions and storing data may all be conventional in construction and operation.

Upstream of this portion A of the apparatus there is a polarizing portion B. Here too the pipeline 10 is made of non-magnetic material although electrically conducting material such as aluminium or stainless steel may be used. Magnets 13 provide a magnetic field to polarize resonant nuclei in the liquid flowing in the pipeline 10, before the liquid reaches the magnetic resonance portion A. These magnets may be made of material with so-called high-temperature superconducting properties (superconductivity above 77 K) such as yttrium barium copper oxide (YBCO), bismuth strontium calcium copper oxide (BSCCO) and the materials mentioned in W02007/045929 and in Coombs et al, Superconductor Sci. & Tech. Volume 21, article 034001 (2008). The portion C is a trapping section for magnetizable material in the flowing fluid. Possible embodiments of the trapping section C will next be described.

Figure 2:
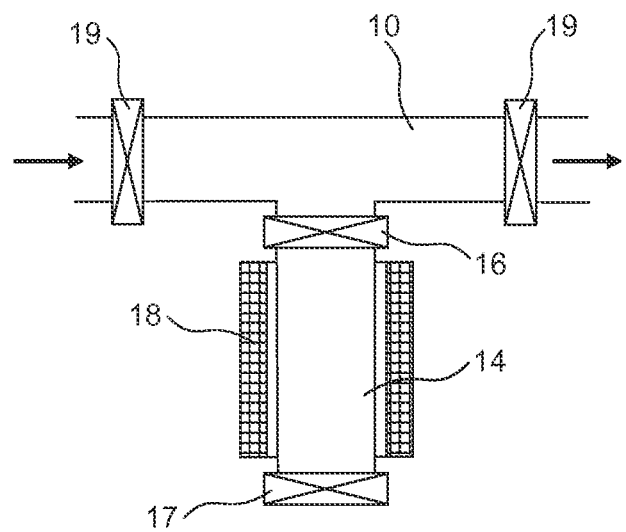
FIG. 2 shows one form of trap.

FIG. 2 shows a simple possibility for trapping magnetizable solids. A branch pipe 14 is connected to the pipeline 10 through a gate valve 16 and is closed at its other end by gate valve 17. The branch pipe 14 is surrounded by a solenoid coil 18. In operation with valve 16 open, valve 17 closed and the solenoid coil 18 energised, the magnetic field within the solenoid coil attracts magnetizable solids out of the fluid stream in the pipeline 10 into the branch pipe 14. Periodically the valve 16 is closed, the coil 18 is turned off and magnetizable solids which have collected in the branch pipe 14 are discharged through valve 17. During this removal of accumulated magnetizable solids, flow along the pipeline 10 may be temporarily halted by closing valves 19.

Figure 3:
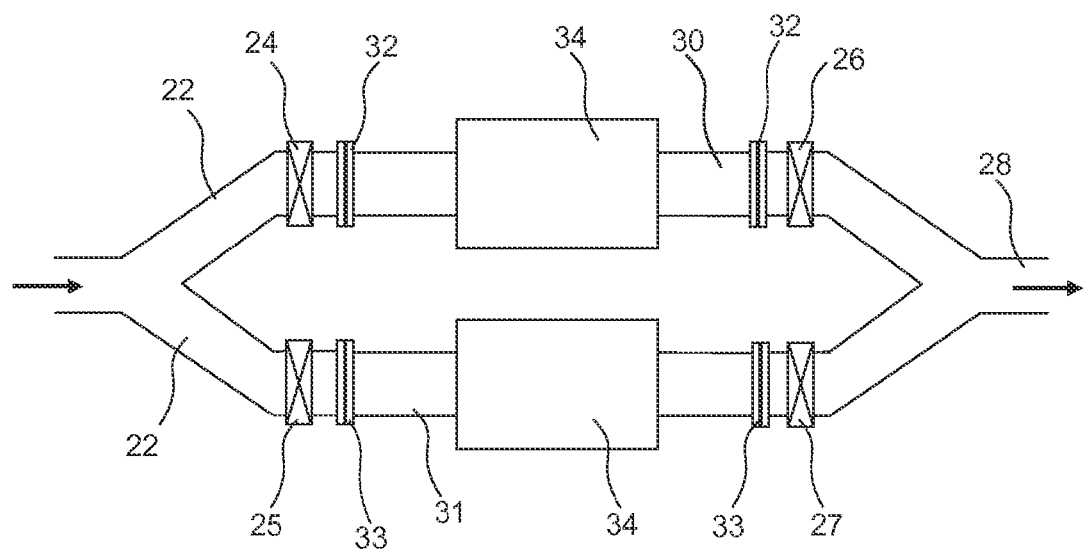
FIG. 3 shows a trapping section with traps in parallel.

FIG. 3 shows a possible arrangement of the trapping section C with traps in parallel. The incoming pipeline splits into two parts 22 which lead to valves 24, 25. Further on the two flow paths pass through valves 26, 27 and then rejoin. Flow in the rejoined path 28 continues into the polarizing section B and the magnetic resonance section A. Between the valves 24 and 26 and between the valves 25 and 27 there are lengths of pipe 30, 31 made of non-magnetic material such as aluminium or stainless steel and attached at flanges 32, 33. These lengths of pipe 30, 31 pass through magnetic fields transverse to the pipe created by pairs of magnets, one above and one below the pipe. The magnets above the pipes are indicated 34 in FIG. 3. While flow is passing through a pipe 30 or 31, the magnetic field draws any magnetizable contaminants to the pipe wall and holds them there. Thus, each length of pipe 30, 31 functions as a trap for magnetizable contaminants.

The valves 24-27 are used to direct flow alternately through the lengths of pipe 30 and 31. So, when valves 24 and 26 are open and flow passes through pipe 30, the valves 25 and 27 may be closed. The length of pipe 31 can then be temporarily detached by unbolting at the flanges 33, removed from the magnetic field, cleaned out and replaced. Subsequently, when valves 25 and 27 are open to direct flow through pipe 31, the valves 24 and 26 can be closed, allowing pipe 30 to be unbolted at flanges 32, removed, cleaned out and replaced.

Figure 4:
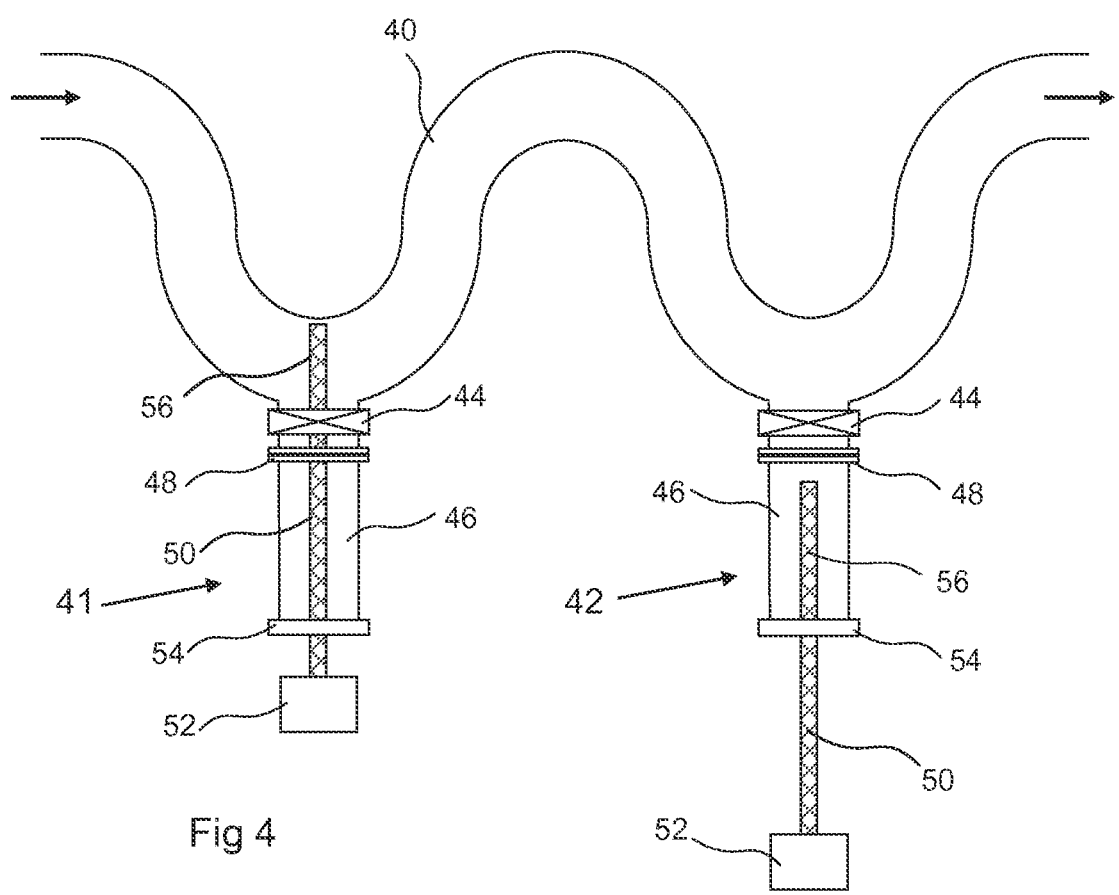
FIG. 4 shows a trapping section with traps in series.

FIG. 4 shows another possible arrangement for the trapping section C. The pipeline 40 follows a serpentine path and has two traps 41, 42 in sequence at low points of the pipeline. Each of these traps has a gate valve 44 opening and closing connection between the pipeline 40 and a length of pipe 46 connected at flanges 48. To provide a magnetic field for trapping magnetizable contaminants, a probe consisting of rod shaped steel pole piece 50 attached to a permanent magnet 52 is mounted so that the pole piece 50 extends through a seal 54 into the pipe 46.

Each probe is movable between two positions. As shown in the trap 41 at the left of FIG. 3, the probe can be pushed inwardly towards the pipeline 40 so that the distal part 56 of the pole piece 50 projects through the gate valve 44 into the pipeline 40. In this position the magnetic field from the magnet 52 attracts any magnetizable material in the flowing stream onto the pole piece 50 and holds them on it.

When it is desired to remove accumulated contaminants from one of the traps, the probe is withdrawn longitudinally to a position as shown in the trap 42 at the right of FIG. 3. The distal part 56 of the pole piece 50 has moved down into the pipe 46, taking accumulated magnetizable material with it. The valve 44 can then be closed and the pipe 46 can be detached at the flanges 48 allowing the pipe 46 and the probe 50, 52 to be removed, cleaned of accumulated magnetizable material and then replaced.

The two traps 41, 42 are operated alternately. At all times one or other of the traps has its magnetic pole piece 50 pushed in, as shown in trap 41 at the left of FIG. 3, so that it can attract and retain magnetizable material. Periodically, the probe 52, 50 of one or other of the two traps is moved to the position as shown by the trap 42, for the accumulated magnetizable material to be removed from it.

Figure 5:
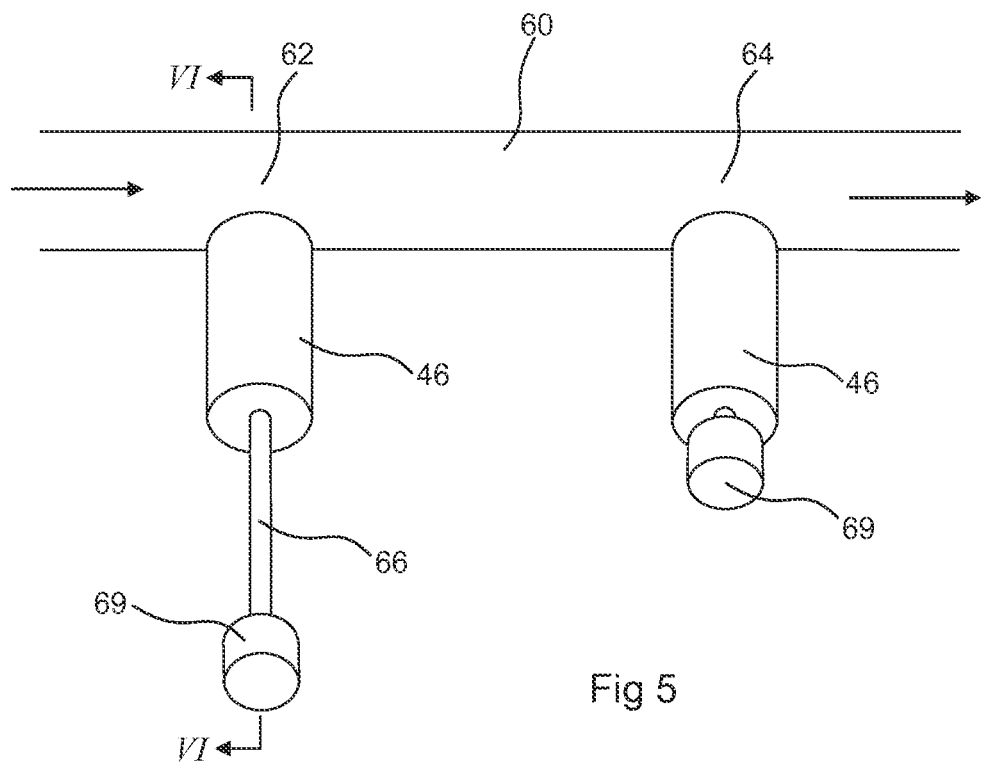
FIG. 5 is a side view of a length of pipeline with two trapping positions.
Figure 6:
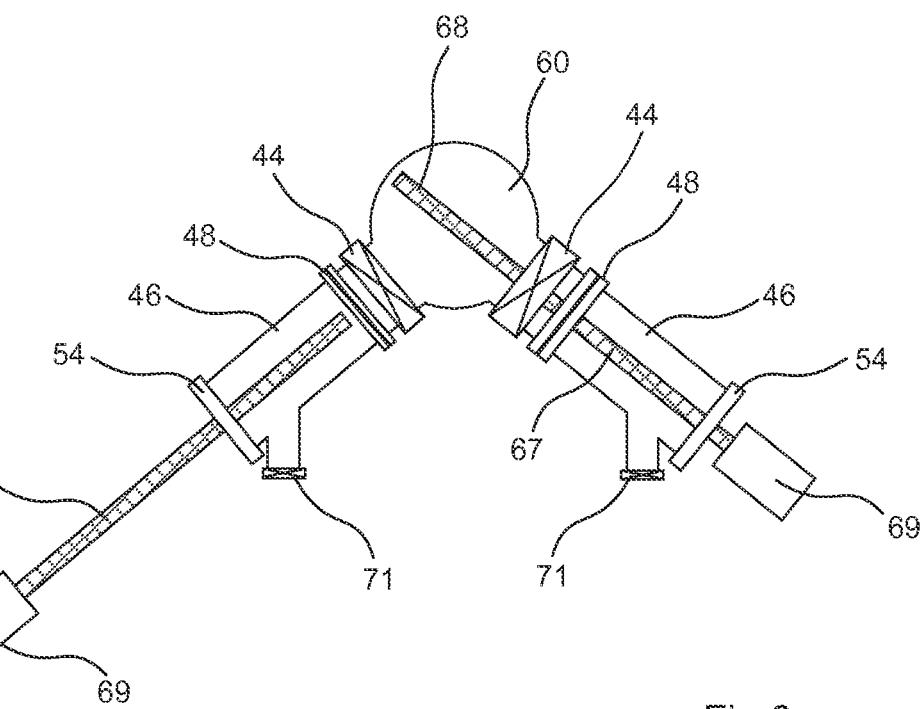
FIG. 6 is a cross section on line VI-VI of FIG. 5.

FIGS. 5 and 6 show a further possibility for a trapping section C. A pipeline 60 carrying flow in the direction shown by arrows has two traps at position 62 and two more at position 64. FIG. 6 is a cross section at position 62 showing that the two traps at this position extend downwardly at an angle at each side of the pipeline 60. The traps are somewhat similar to the traps in FIG. 4. Each trap communicates with the pipeline 60 through a gate valve 44 and has a pipe 46 attached at flanges 48. The traps have probes comprising electromagnets 69 and pole pieces 66, 67 which extend through seals 54. The probes are movable between two positions. A pushed-in position is shown by pole piece 67 and also at the right of FIG. 5. In this position the distal part 68 of the pole piece extends across the pipeline 60 and its magnetic field attracts and holds any magnetizable solid material. The pole piece can also be drawn back into the pipe 46, through gate valve 44, as illustrated by pole piece 66. When the pole piece is drawn back, as in the case of pole piece 66, it carries accumulated magnetizable material with it into the pipe 46. After a pole piece has been withdrawn as shown by pole piece 66, the gate valve 44 is closed and the electromagnet 69 for that pole piece is switched off. Accumulated magnetizable material on the pole piece 66 then falls off into the pipe 46, and can be discharged through a valve 71.

The four traps are operated in a sequence such that at any time at least one trap has its pole piece pushed in and extending across the pipeline 60. While the pole pieces of the two traps at position 62 are moved to allow one of the traps to be cleaned out, one trap at position 64 always has its pole piece pushed in and functioning to collect magnetizable material. Correspondingly one trap at position 62 has its pole piece in the pushed in position throughout the time that pole pieces of the traps at position 64 are moved between their two positions.

Figure 7:
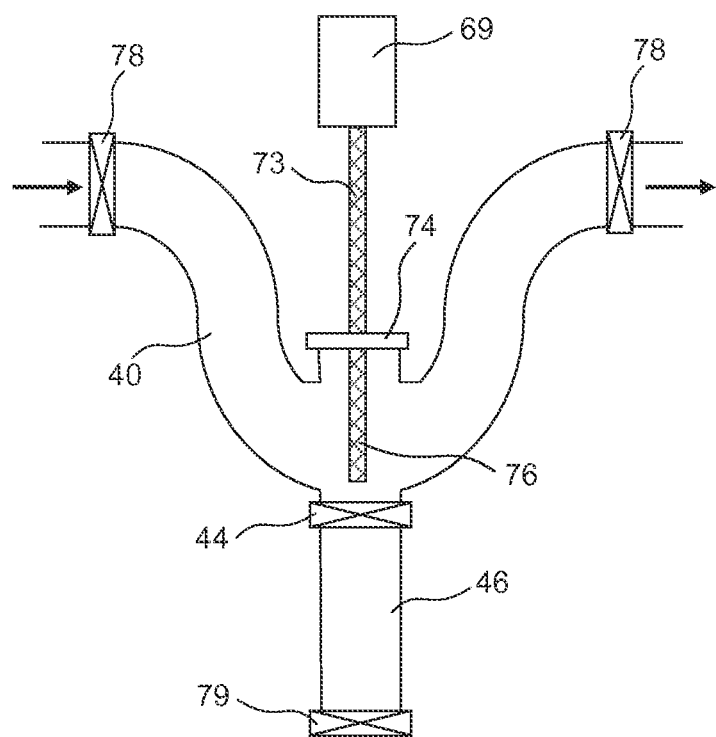
FIG. 7 shows another form of trap.

FIG. 7 shows a single trap with some resemblance to the traps in FIG. 4. As in FIG. 3, a low point of pipeline 40 is connected to a branch pipe 46 through a gate valve 44. A probe consisting of a pole piece 73 and an electromagnet 69 is located above the pipeline and extends into the pipeline through a seal 75, so that the distal part 76 of the pole piece 73, magnetised by the electromagnet 69 arrests and holds magnetizable solids entrained in the flow stream along the pipeline 40. Periodically, flow is stopped by closing valves 78. The pole piece 73 and the electromagnet 69 are lowered, so that the distal part 76 of the pole piece carrying magnetizable solids accumulated on it passes through the open valve 44 into the branch pipe 46. The electromagnet 69 is then switched off, so that the magnetizable solids fall from the pole piece 73 into the branch pipe. The pole piece and electromagnet are then raised back to the position shown, with the electromagnet still switched off. The valve 44 is closed and the magnetizable solids in the branch pipe 46 are discharged by opening the valve 79.

Figure 8:
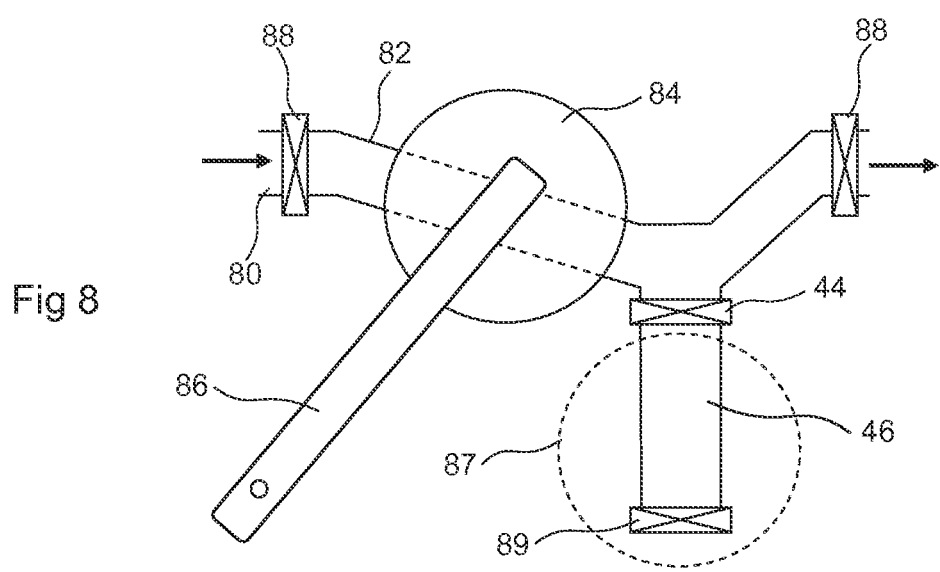
FIG. 8 shows another form of trap.

FIG. 8 shows a further possibility for a single trap. The pipeline 80 has a downwardly inclined tubular section 82 at the lower end of which a branch pipe 46 is connected to the pipeline 80 through a gate valve 44. A magnetic field to arrest magnetizable solids is provided by a pair of permanent magnets 84 located at either side of the inclined section 82. These magnets 84 are supported on pivoted arms 86. Periodically, to remove accumulated magnetizable solids from the inclined section 82, flow is stopped with by closing valves 88 and the arms 86 and magnets 84 are swung to put the magnets 84 at the position shown by a dotted circle 87, with the magnetic field now extending through the branch pipe 46. This movement of the magnetic field allows and assists the accumulated magnetizable solids to slide down the inclined section 82 into the branch pipe 46. The gate valve 44 is then closed, the magnets 84 are then swung back to their original position and the magnetizable solids are discharged from the branch pipe 46 by opening valve 89.

It will be appreciated that the diagrams shown here are schematic and do not show the equipment used to move the magnets 52, 69 and pole pieces 50, 66, 67 73 between positions, nor the mechanical handling equipment used to move detached pipes 30, 31 or 46. Many modifications are possible and features used in one embodiment illustrated here may be utilised in another embodiment. Specifically, the single traps shown in FIGS. 2, 7 and 8 could be used in an arrangement with two traps in parallel or in sequence. Any of the trapping sections shown in FIGS. 2 to 8 could be used with the resonance section A but without a polarising section B if so desired. Magnetic fields of any of the traps could be provided by electromagnets instead of permanent magnets, or could be provided by movably mounted permanent magnets in place of electromagnets. All such modifications are intended to be included within the scope of this disclosure.

The invention claimed is:

1. Nuclear magnetic resonance apparatus for measuring properties of a fluid stream flowing within a pipeline, comprising one or more magnet systems for applying one or more magnetic fields to the fluid stream and means for inducing and observing magnetic resonance within the fluid stream as it passes through a said magnetic field,
   wherein the apparatus comprises one or more traps having a magnetic field to attract and hold solid magnetizable material and an exit path for the removal of the solid magnetizable material and
   wherein said one or more trap comprises a branch pipe from the pipeline and said magnetic field is positioned to attract solid magnetizable material from the fluid stream into the branch pipe.

2. Apparatus according to claim 1 wherein said at least one trap comprises a tubular section made of non-magnetic material and conveying the fluid stream and one or more magnets positioned to provide a magnetic field within the tubular section.

3. Apparatus according to claim 1 comprising at least two traps and valves for selectively directing the fluid stream through one or other of the traps.

4. Apparatus according to claim 1 comprising at least two traps, each of which comprises a tubular section made of non-magnetic material, valves for selectively directing the fluid stream through one or other of the traps and one or more magnets positioned to provide a magnetic field within each tubular section.

5. Apparatus according to claim 1 wherein said at least one trap comprises a magnetic pole piece extending into the pipeline.

6. Apparatus according to claim 1 comprising at least two traps, wherein each said trap comprises a branch pipe from the pipeline and a said magnetic field is positioned to attract solid magnetizable material from the fluid stream into the branch pipe.

7. Apparatus according to claim 1 wherein said at least one trap comprises a branch pipe providing an exit path for removal of solid magnetizable material, and a valve to open and close communication between the pipeline and the branch pipe.

8. Apparatus according to claim 1 wherein said at least one trap comprises a branch pipe for removal of solid magnetizable material, a valve to open and close communication between the pipeline and the branch pipe and a magnetic pole piece movable between a position in which the pole piece projects through the valve into the pipeline and a position in which the pole piece is withdrawn through the valve into the branch pipe.

9. Apparatus according to claim 1 comprising at least two traps, wherein each said trap comprises a branch pipe providing an exit path for removal of solid magnetizable material, and a valve to open and close communication between the pipeline and the branch pipe.

10. Apparatus according to claim 9 wherein each said trap comprises a branch pipe for removal of solid magnetizable material, a valve to open and close communication between the pipeline and the branch pipe and a magnetic pole piece movable between a position in which the pole piece projects through the valve into the pipeline and a position in which the pole piece is withdrawn through the valve into the branch pipe.

11. A method of intercepting solid magnetizable material entrained in a liquid flow in a pipeline upstream of a magnetic resonance spectrometer, comprising
    directing the flowing liquid upstream of the spectrometer through at least one trap having a magnetic field to attract and hold solid magnetizable material, and an exit path for the removal of the solid magnetizable material; wherein said one or more trap comprises a branch pipe from the pipeline and said magnetic field is positioned to attract solid magnetizable material from the fluid stream into the branch pipe.

12. A method according to claim 11 wherein the flowing fluid comprises oil produced from an underground reservoir.

13. A method according to claim 12 comprising directing the liquid flow through at least one of a plurality of said traps, and periodically removing solid magnetizable material from a said trap while the liquid flows through another said trap.

* * * * *